(12) United States Patent
Furmanski et al.

(10) Patent No.: US 9,132,280 B2
(45) Date of Patent: Sep. 15, 2015

(54) USE OF FUSAROCHROMANONE AND ITS DERIVATIVES IN THE DIAGNOSIS AND TREATMENT OF CANCER AND OTHER DISEASES

(71) Applicant: University of South Carolina, Columbia, SC (US)

(72) Inventors: Brian Furmanski, Memphis, TN (US); Roy E. Wuthier, Columbia, SC (US); John W. Fuseler, Jr., Columbia, SC (US)

(73) Assignee: University of South Carolina, Columbia, SC (US)

( * ) Notice: Subject to any disclaimer, the term of this patent is extended or adjusted under 35 U.S.C. 154(b) by 154 days.

(21) Appl. No.: 13/728,357

(22) Filed: Dec. 27, 2012

(65) Prior Publication Data

US 2014/0031739 A1   Jan. 30, 2014

Related U.S. Application Data

(62) Division of application No. 12/422,590, filed on Apr. 13, 2009, now Pat. No. 8,344,020.

(60) Provisional application No. 61/123,818, filed on Apr. 11, 2008, provisional application No. 61/123,819, filed on Apr. 11, 2008.

(51) Int. Cl.
*A61K 31/35* (2006.01)
*A61N 5/06* (2006.01)
*A61K 41/00* (2006.01)

(52) U.S. Cl.
CPC ............... *A61N 5/062* (2013.01); *A61K 31/35* (2013.01); *A61K 41/0057* (2013.01)

(58) Field of Classification Search
None
See application file for complete search history.

(56) References Cited

U.S. PATENT DOCUMENTS

| | | |
|---|---|---|
| 5,932,611 A | 8/1999 | Wuthier et al. |
| 6,225,340 B1 | 5/2001 | Wuthier et al. |
| 6,660,765 B2 | 12/2003 | Wuthier et al. |
| 7,078,433 B2 | 7/2006 | Wuthier et al. |
| 2001/0011100 A1* | 8/2001 | Wuthier et al. ............... 514/456 |
| 2004/0092580 A1 | 5/2004 | Wuthier et al. |

FOREIGN PATENT DOCUMENTS

WO    WO 03/024526    * 3/2003    ............... A61N 5/06

OTHER PUBLICATIONS

Fisher (Acta Derm Venereol 57(4):345-350, 1977; Abstract only).*
ACD/PhysChem Predictor, version 11.00, Advanced Chemistry Development, Inc., Toronto ON, Canada, www.acdlabs.com, 2007.

Allen, N. K.; Jevne, R. L.; Mirocha, C. J.; Lee, Y. W.; The Effect of a Fusarium roseum Culture and Diacetoxyscirpenol on Reproduction of White Leghorn Females. *Poul. Sci.* 1982, 61, 2172-2175.
Altenburg, G. A.; Vanoye, C. G.; Horton, J. K,; Reuss, L., Unidirectional fluxes of rhodamine 123 in multidrug-resistant cells: Evidence against direct drug extrusion from the plasma membrane. *Proc. Natl. Acad. Sci.* 1994, 91, 4654-4657.
Bemporad, D,; Luttmann, C.; J.W. Essex, Computer Simulation of Small Molecule Permeation across a Lipid Bilayer: Dependence on Bilayer Properties and Solute Volume, Size, and Cross-Sectional Area. *Biophys. J.* 2004, 87, 1-13.
Bulychev, A.; Trouet, A., Uptake and intracellular distribution of neutral red in cultured fibroblasts. *Exp. Cell. Res.* 1978, 115, 343-355.
Dréau, D.; Foster, M.; Hogg, M.; Culberson, C,; Nunes, P.; Wuthier, R E., Inhibitory effects of fusarochromanone on melanoma growth. *Anti-Cancer Drugs* 2007, 18, (8), 897-904.
Eytan, G. D.; Regev, R.; Oren, G.; Assaraf, Y. G., The Role of Passive Transbilayer Drug Movement in Multidrug Resistance and Its Modulation. *J. Biol. Chem.* 1996, 271, (22), 12897-12902.
Fuseler, J. W.; Merrill, D. W.; Grisham, M. B.; Wolf, R. E., Analysis and quantitation of NF-kB nuclear translocation in tumor necrosis factor alpha activated vascular endothelial cells. *Microsc. Microanal.* 2006, 12, 269-276.
Fuseler, J. W,; Millette, C. F.; Davis, J. M.; Wayne Carver, W., Fractal and image analysis of morphological changes in the actin cytoskeleton of neonatal caradaic fibroblasts in response to mechanical stretch. *Microsc. Microanal.* 2007, 13, 128-132.
Horobin, R. W,; Stockert, J, C.; Rashid-Doubell, F., Fluorescent cationic probes for nuclei of living cells: why are they selective? A quantitative structure-activity relations analysis. *Histochem Cell Biol* 2006, 126, 165-175.
Kramer, S. D., Absorption prediction from physicochemical parameters. *Pharma. Sci. & Tech. Today* 1999, 2, (9).
L.D. Mayer, M. B. B., P.R. Cullis, Uptake of adiamycin into large unilamellar vesicles in response to p pH gradient. *Biochimica et Biophysica Acta-Biomembranes* 2003, 857, (1), 123-126.
Lee, Y.-W.; Mirocha, C. J.; Shroeder, D,; Walser, M., TDP-1, a toxic component causing tibial dyschondroplasia in broiler chickens, and trichothecenes from Fusarium roseum, Graminerarum. *Appl Environ Microbiol* 1985, 50, (1), 15.
Lipinski, C. A.; Lombardo, F.; Dominy, B. W.; Feeney, P. J., Experimental and Computational approaches to estimate solubility permeability in drug discovery and development settings. *Adv. Drug Delivery Rev.* 2001, 46, 3-26.
Minervini, F.; Lucivero, G.; Visconti, A.; Bottalico, C., Immunomodulatory effects of Fusarochromanones TDP-1 and TDP-2. *Natural Toxins* 1992, 1, (15).
Nie, D. Effects of fusarochromanone on endothelial cells: Implications in deficient vascularization in pathogenesis of avian tibial dyschondroplasia. Ph.D Thesis, Univ. of South Carolina, Columbia, 1997.

(Continued)

*Primary Examiner* — Craig Ricci
(74) *Attorney, Agent, or Firm* — Dority & Manning, P.A.

(57) ABSTRACT

A method of photodynamic therapy to treat diseased cells in an animal is generally provided. According to the method, 5-amino-2,2-dimethyl-6-[3'-(R,S)amino-4'-hydroxy-butan-1-one]-2,3-dihydro-4H-1-benzopyran-4-one or an analog thereof is administered to the animal such that the 5-amino-2,2-dimethyl-6-[3'-(R,S)amino-4'-hydroxy-butan-1-one]-2,3-dihydro-4H-1-benzopyran-4-one or an analog thereof accumulates in the diseased cells. Then, the diseased cells containing 5-amino-2,2-dimethyl-6-[3'-(R,S)amino-4'-hydroxy-butan-1-one]-2,3-dihydro-4H-1-benzopyran-4-one or an analog thereof is exposed to light energy (e.g., ultraviolet light).

7 Claims, 8 Drawing Sheets

(56) References Cited

OTHER PUBLICATIONS

OECD Guideline for Testing of Chemicals. Paris, 1987.
Palm, K.; Stenberg, P.; Luthman, K; Artursson, P.; Polar Molecular Surface Properties Predict the Intestinal Absorption of Drugs in Humans. *Pharma. Res.* 1997, 14, (5), 568-571.
Principles of Medicinal Chemistry, William O. Foye, Thomas L. Lemke, and David A. Williams, editors, 4th ed., 1995.
Rashid-Doubell, F.; Horobin, R. W., Selection of Fluorescent Golgi Complex Probes Using Structure-Activity Relationship Models. In *Biotechnology Applications of Microinjection, Microscopic Imaging, and Fluorescence,* al., P. H. B. e., Ed. Plenum Press: 1993.
Remington's Pharmaceutical Science, 17th edition, 1985.
Rogers, J. A.; Fuseler, J. W., Regulation of NF-kB activation and nuclear translocation by exogenous nitric oxide (NO) donors in the THF-á activated vascular endothelial cells. *Nitric Oxide* 2007, 16, 379-391.
Sato, T.; Hashizume, M.; Hotta, Y.; Okahata, Y., Morphology and proliferation of B16 melanoma cells in the presence of lanthanoid and $Al^{3+}$ions. *BioMetals* 1998, 11, 107-112.
Seidler, J,; McGovern, S. L.; Doman, T. N.; Shoichet, B, K., Identification and Prediction of Promiscuous Aggregating Inhibitors among Known Drugs. *J. Med. Chem.* 2003, 46, 4477-4486.
Simon, S.; Roy, D.; Schindler, M., Intracellular pH and the control of multidrug resistance. *Proc. Natl. Acad. Sci.* 1994, 91, (1128-1132).
Spoelstra, E, C.; Westerhoff, H. V.; Dekker, H.; Lankelma, J., Kinetics of daunorubicin transport by P-glycoprotein of intact cancer cells, *Eur. J. Biochem.* 1992, 207, 567-579.
Testa, B.; Caldwell, J., Prodrugs Revisited: The "Ad Hoc" Approach as a Complement to Ligand Design. *Med. Res. Rev.* 1996, 16, (3), 233-241.
Vattulainen, I., Molecules Dancing In Membranes. *Diffusion-Fundamentals* 2005, 2, (113.1-113.15).
Veber, D. F.; Johnson, S. R.; Cheng, H,-Y.; Smith, B. R.; Ward, K. W.; Kopple, K. D., Molecular Properties That Influence the Oral Bioavailbility Of Drug Candidates. *J. Med. Chem* 2002, 45, 2615-2623.
Walser, M, M.; Allen, N. K.; Mirocha, C. J.; Hanlon, G. F.; Newman, J. A., Fusarium-induced osteochondrosis (tibial dyschondroplasia) in chickens, *Vet. Pathol.* 1982, 19, (5), 544.
Walter, J. R, J,; Berns, M. W., *Digital Image Processing and Analysis. In Video Microscopy.* New York and London: Plenum Press: 1986; pp. 327-392.
Warburg, O., On the Orgin of Cancer Cells. *Science* 1956, 123, (3191), 309-314.
Xie, W. P.; Mirocha, C. J.; Pawlosky, R. J.; Wen, Y. C.; Xu, X, G., Biosynthesis of fusarochromanone and its monoacetyl derivative by Fusarium equiseti, *Appl. Environ. Microbiol.* 1989, 55, (4), 794.
Yang, W.C.; Stasser, F.F., Mechanism of drug-induced vacuolization in tissue culture, *Exp. Cell. Res.* 1965, 38, 495-506.
USC Chemist (pp. 1-16, Fall 2003).
Melanoma and Other Skin Cancers In-Depth (available online at www.discoveryhealth.com, Jun. 7, 2006).
Stille (Invisible Exposure: The Science of Ultraviolet Rays, pp. 12-13, 2010).

* cited by examiner

Figure 5
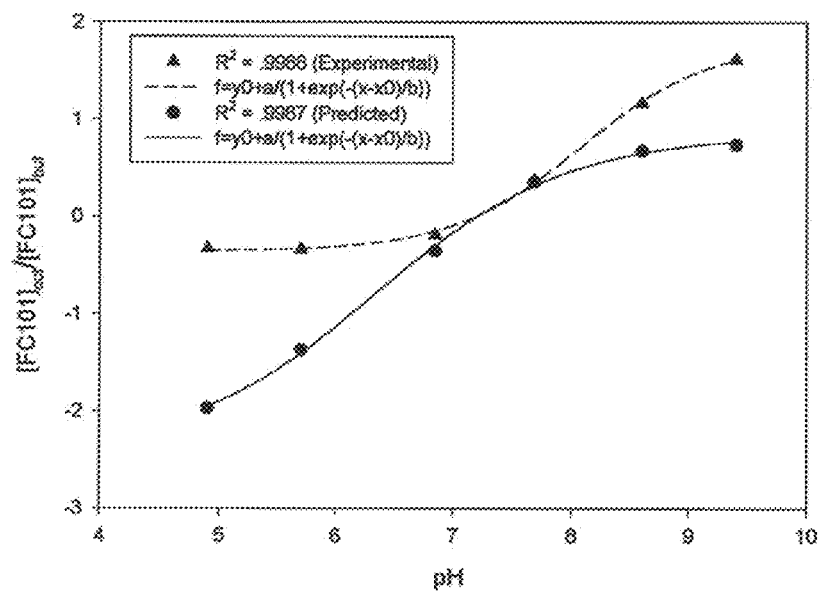
Supplemental Figures 5A and 5B
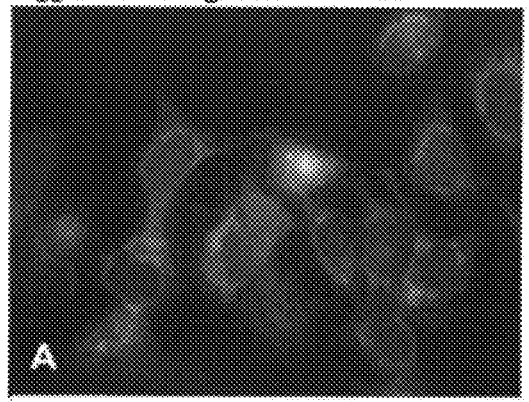
Figure 5A
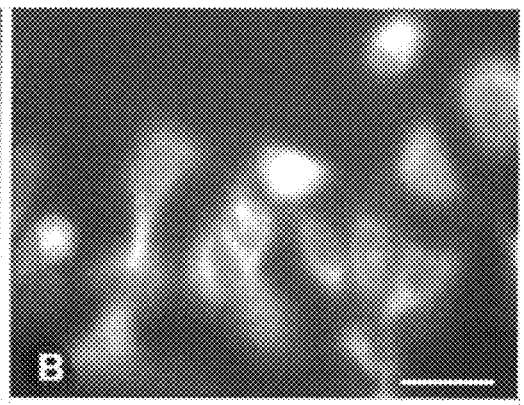
Figure 5B

USE OF FUSAROCHROMANONE AND ITS DERIVATIVES IN THE DIAGNOSIS AND TREATMENT OF CANCER AND OTHER DISEASES

PRIORITY INFORMATION

The present application is a divisional application of and claims priority to U.S. patent application Ser. No. 12/422,590, issued as U.S. Pat. No. 8,344,020, titled "Use of Fusarochromanone and Its Derivatives in the Diagnosis and Treatment of Cancer and other Diseases" of Furmanski, et al. filed on Apr. 13, 2009, and claims priority to U.S. Provisional Patent Application Ser. No. 61/123,818 filed on Apr. 11, 2008 titled "Use of Fusarochromanone and Its Derivatives in the Diagnosis and Treatment of Cancer and other Diseases" and U.S. Provisional Patent Application Ser. No. 61/123,819 filed on Apr. 11, 2008 titled "Novel Method for the Application of Fluorescent Compounds in Photodynamic Therapy". The disclosures of all these applications are incorporated by reference herein.

BACKGROUND OF THE INVENTION

The use of light in the treatment of various skin diseases has been around for centuries. This field termed phototherapy uses a combination of small molecules that can absorb light in the visible, UV-A, and near-infrared range. Phototherapy is comparable to radiotherapy in its efficacy. However unlike radiotherapy and chemotherapy, phototherapy lacks the non-specific toxicity seen in radiotherapy and chemotherapy and because of this, phototherapy can be given on more regular intervals.

Photodiagnostic therapy (PDT) is an experimental technology that relies on the ability of fluorescent small molecules to preferentially accumulate in diseased tissues. Due to this preferential retention, it is possible to distinguish between normal and diseased tissue. It is thought that these small molecules in tumorgenic tissues may accumulate due to a decrease in intracellular pH, an increase in low density lipoproteins, and abnormal membrane composition[1].

It is generally accepted that small nonpolar molecules can pass through the plasma membrane of a cell by simple diffusion[3]. Evidence for this has been described in the uptake of adriamycin, quinone, and rhodamine 123 in unilamellar and transbilayer vesicles[4,5]. Simple diffusion has also been used to describe the uptake of doxorubicin, daunorubicin, and rhodamine 123 in cultured transformed and normal cells[1,6,7].

Photodynamic therapy (PDT) is an emerging minimally invasive therapy for the treatment of cancer, age-related macular degeneration, psoriasis and a host of other chronic diseases. PDT employs the use of photosensitizing agents in combination with light to disrupt cellular functions, which ultimately leads to cell death. The intracellular location of photosensitizing agents also plays critical role in the mode of action in cellular toxicity. Most photosensitizers used in clinical, and experimental treatment of cancer are localize in cytoplasmic organelles of a cell.[8] Photosensitizing agents are compounds that absorb a specific wavelength of light which then reacts with molecular oxygen to generate a reactive oxygen species. These reactive oxygen species such as $H_2O_2$, NO, and $^-OH$ are the true perpetrators of the cellular toxicity seen in PDT.

Psoralen is commonly used in PDT to treat skin diseases (e.g., Eczema, Psoriasis and Vitiligo, and mycosis fungoides). However, psoralen is not a chemotherapeutic agent by itself, and therefore is not effective without the application of energy in the form of light.

Although great strides have been made in photodynamic therapy, a need exists for a photosensitizing agent that will selectively accumulate in diseased cells and act as a chemotherapeutic agent (even without the application of light).

SUMMARY OF THE INVENTION

Objects and advantages of the invention will be set forth in part in the following description, or may be obvious from the description, or may be learned through practice of the invention.

In general, the present disclosure is directed toward a method of photodynamic therapy to treat diseased cells in an animal. According to the method, 5-amino-2,2-dimethyl-6-[3'-(R,S)amino-4'-hydroxy-butan-1-one]-2,3-dihydro-4H-1-benzopyran-4-one or an analog thereof is administered to the animal such that the 5-amino-2,2-dimethyl-6-[3'-(R,S)amino-4'-hydroxy-butan-1-one]-2,3-dihydro-4H-1-benzopyran-4-one or an analog thereof accumulates in the diseased cells. Then, the diseased cells containing 5-amino-2,2-dimethyl-6-[3'-(R,S)amino-4'-hydroxy-butan-1-one]-2,3-dihydro-4H-1-benzopyran-4-one or an analog thereof is exposed to light energy (e.g., ultraviolet light).

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

For B16 Melanoma Cells:

A—Time 0 (before exposure to FC101). All Cells express weak auto-fluorescence localized predominantly in the perinuclear cytoplasm.

B—Time–10 sec following addition of FC101 (400 nM). The drug has immediately entered the cells and is accumulating in the perinuclear cytoplasm. Accumulation of the drug in the perinuclear region appears asymmetrical, suggesting it may be preferentially localized in the Golgi complex.

C—Time–4 min following addition of FC101. FC101 fluorescence remains largely localized in the perinuclear region and does not appear to spread out into the peripheral and marginal cytoplasm. The cells exhibit little or no morphological changes at this time.

D—Time–20 min following addition of FC101. The distribution and fluorescence of FC101 appears stable with no decrease in intracellular drug fluorescence. The cells also exhibit little or no morphological changes at this time.

For Normal Cardiac Fibroblasts:

E—Time 0. All cells express a minimal auto-fluorescence predominately localized in the perinuclear cytoplasm.

F—Time–10 sec flowing addition of FC101 (400 nM). The cells exhibit no uptake of FC101 with the cytoplasmic fluorescence remaining essentially the same as that seen before exposure to FC101 (E).

G—Time–4 min following addition of FC101. Some of the cells exhibit a minimal increase in cytoplasmic fluorescence due to limited uptake of the drug.

H—Time–20 min following additional of FC101. All cells exhibit a significant increase in intracellular fluorescence due to continued slow uptake of the drug. FC101 appears predominantly localized in the perinuclear cytoplasm. Scale bar=20 μm.

Figure 1:
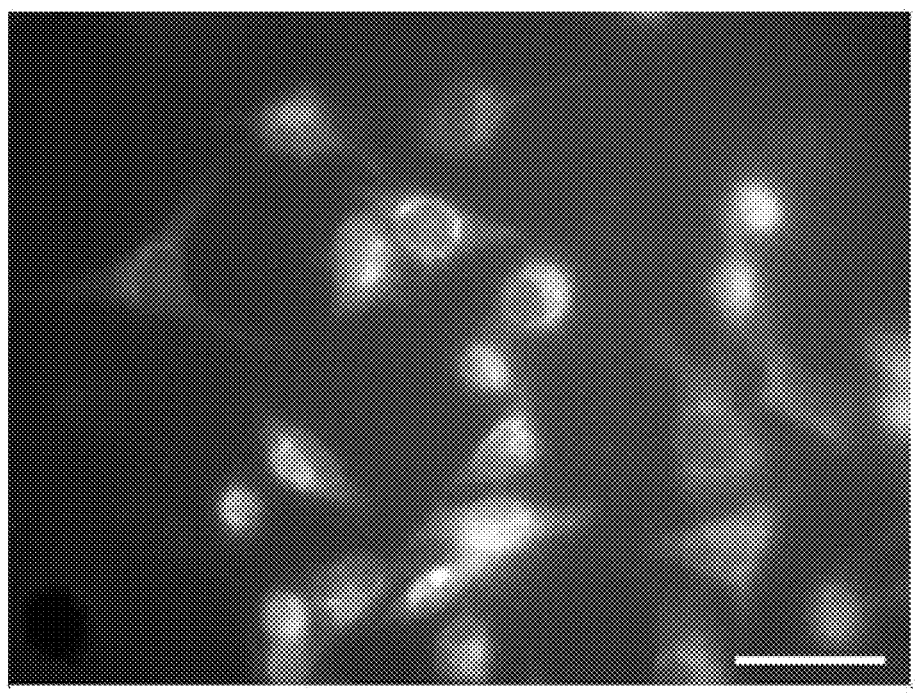
FIG. 1 shows a co-culture monochrome image of B16 melanoma and cardiac myocytes.
Figure 2:
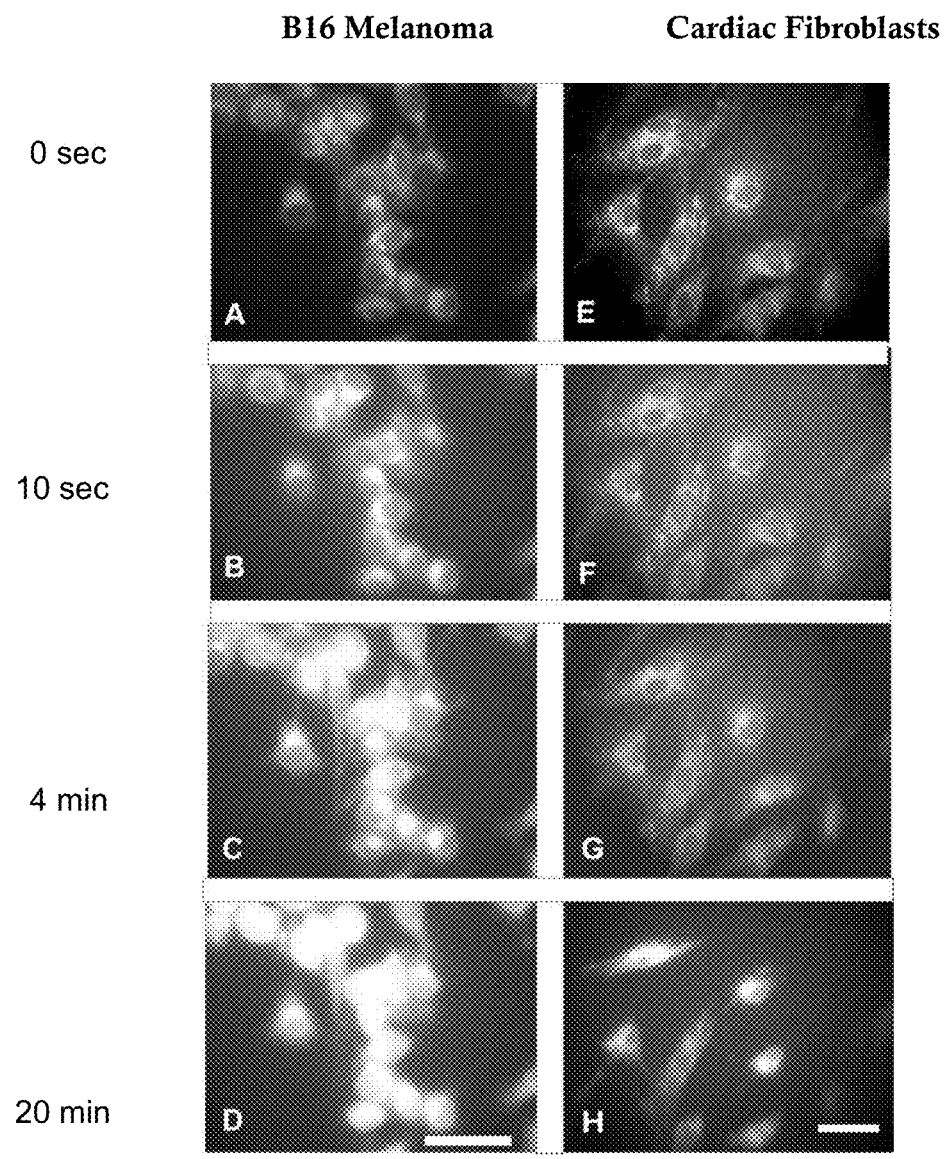
FIG. 2 shows confocal Imaging of FC101 Uptake of B16 Melanoma Cells and normal cardiac fibroblasts.
Figure 2A:
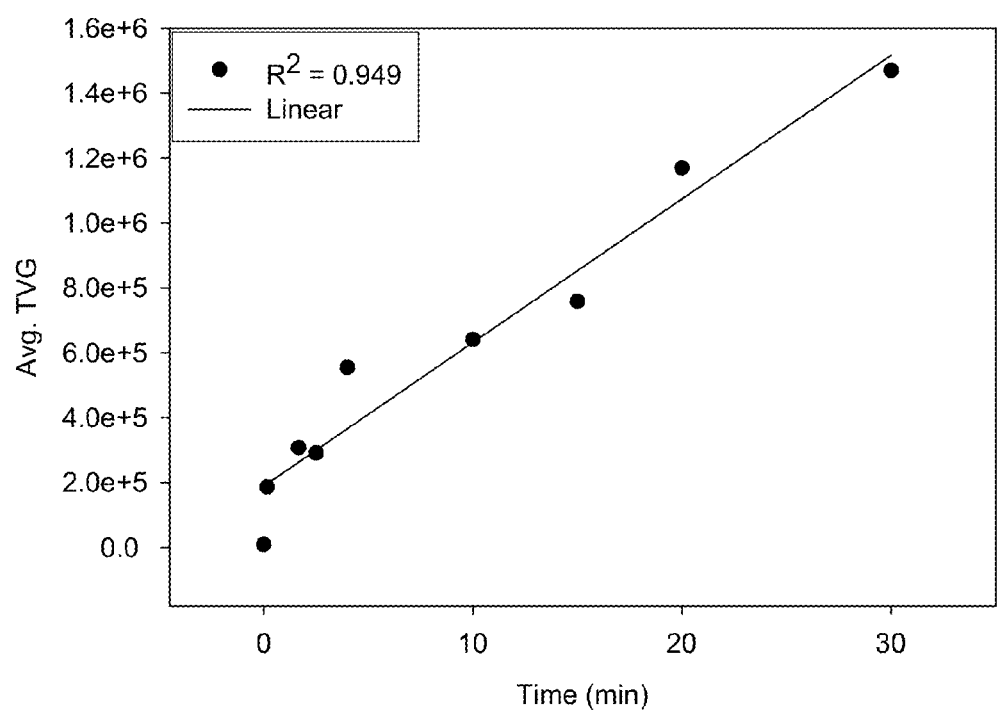

FIG. 2A shows the linear uptake of FC101 in B16 cells.

Figure 2B:
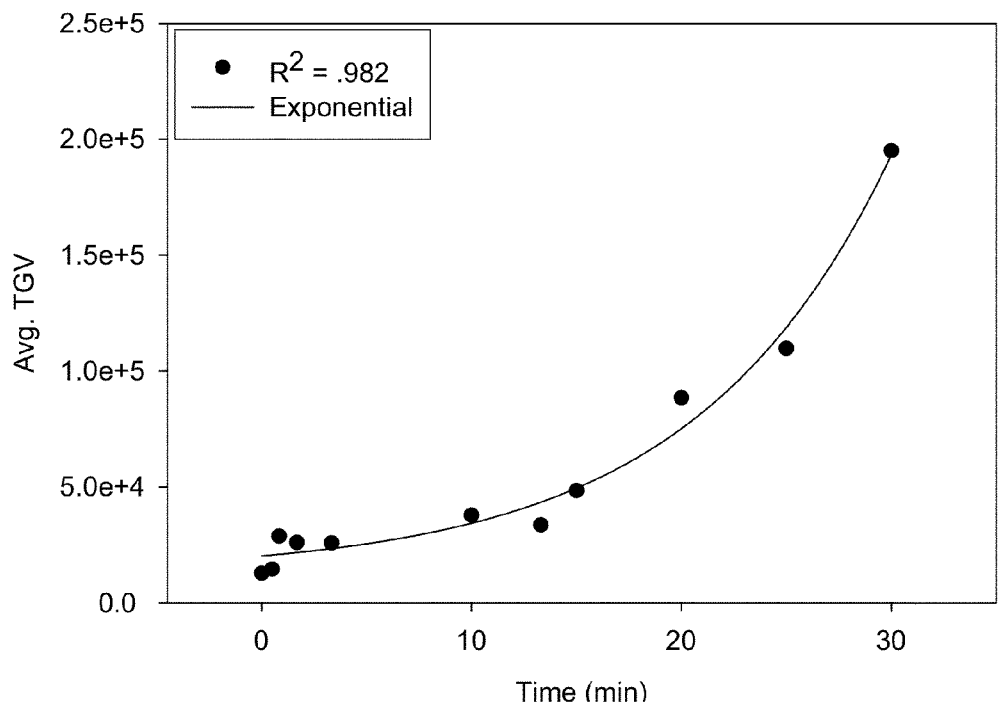

FIG. 2B shows the exponential uptake in normal cardiac fibroblasts.

Figure 3A:
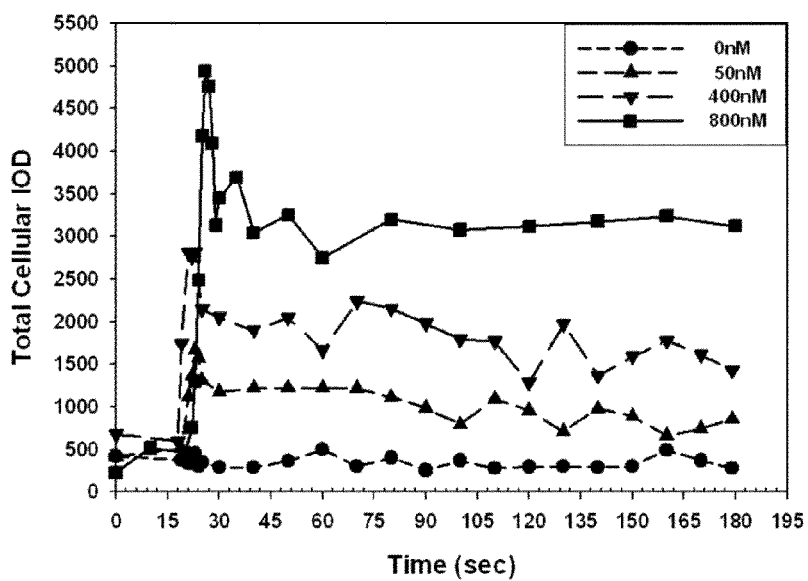

FIG. 3a shows a comparison of the Uptake and Steady-State Concentrations of FC101 in the Cytoplasm of B16 Melanoma Cells. Images of the B16 melanoma were collected at 1 second intervals. FC101 was added to cells at 20 seconds following initiation of the experiment with the capture of image 2. Total cellular integrated optical density was measured for each of the indicated FC101 levels.

Figure 3B:
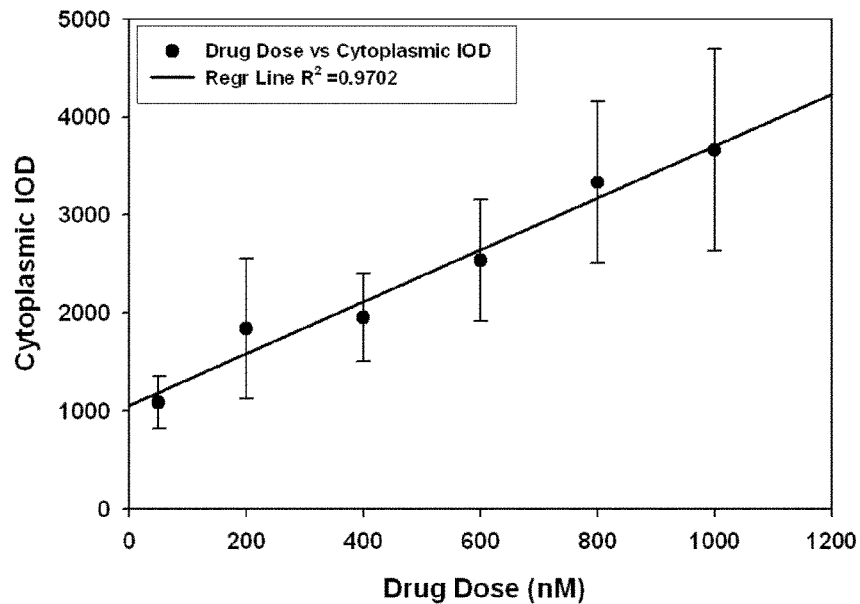

FIG. 3b shows the relationship between Drug Dosage and Steady-State Intracellular Concentration of FC101 in B16 Melanoma Cells. Steady-state IOD levels of FC101 were measured at drug level after 2 min incubation. Note the linear correlation between the initial extracellular concentration of the drug and the cytoplasmic IOD of FC101. These kinetic data suggest the uptake of FC101 in B16 melanoma cells is dependent only the initial concentration of the drug applied to cells, and that uptake appears to be governed by zero-order kinetics.

Figure 4A:
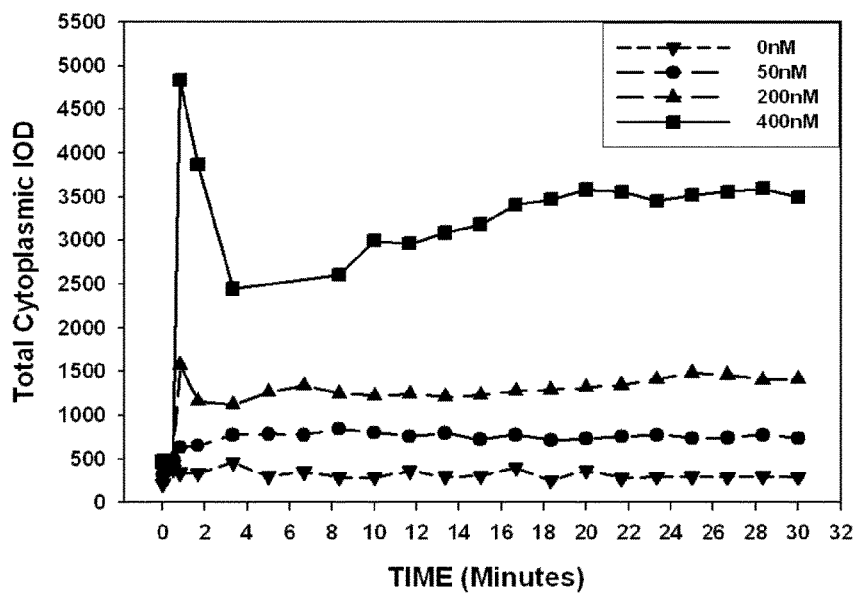
Figure 7:
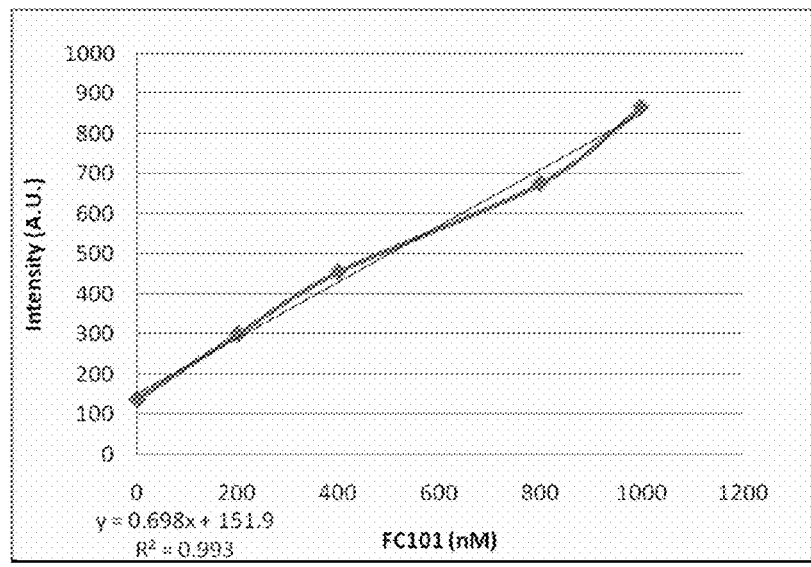

FIG. 4a shows the comparison of the Uptake and Steady-State Concentrations of FC101 in the Cytoplasm of Normal Cardiac Fibroblasts. FC101 was added to cells at 30 seconds following initiation of the experiment with the capture of image 1. Images of the Cardiac Fibroblasts were collected at 10 sec intervals. Total cellular integrated optical density was measured for each of the indicated FC101 levels. Note that the scale is shown in minutes, not in seconds as seen in FIG. 7.

Figure 4B:
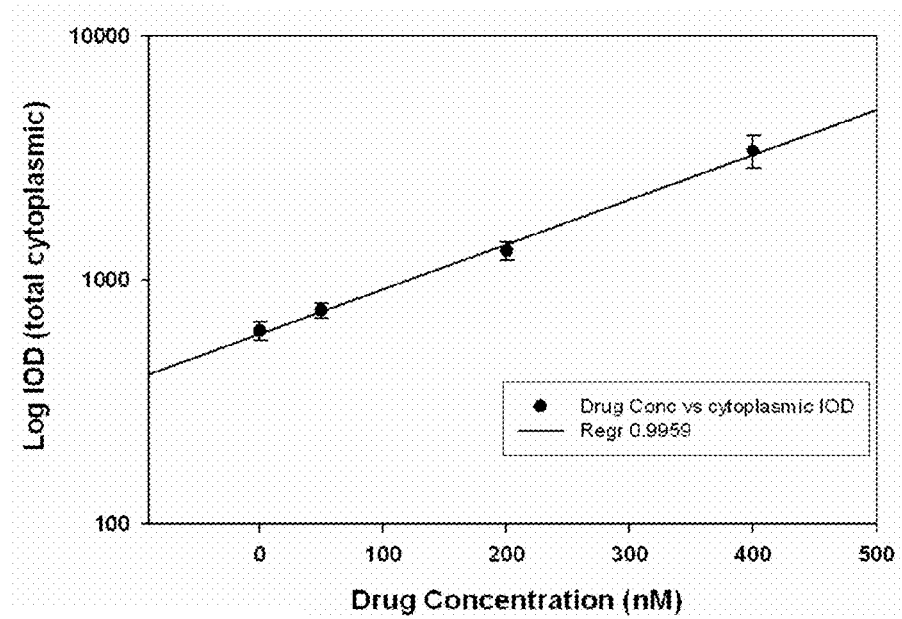

FIG. 4b shows the relationship between Drug Dosage and Steady-State Intracellular Concentration of FC101 in Normal Cardiac Fibroblasts. Steady-state IOD levels of FC101 were measured at drug level after 10 min incubation. The Y-axis is expressed in exponential terms; note the close correlation between the initial extracellular concentration of the drug and the $Log_{10}$ IOD of cytoplasmic FC101. Thus, the intracellular concentration of FC101 follows a non-linear logarithmic correlation with the initial extracellular concentration of the drug. These data suggest that uptake of FC101 in cardiac fibroblasts may be carrier-mediated, in addition to being dependent on the initial concentration of the drug applied to cells.

FIG. 5 shows the comparison of Experimentally Measured and ACD-Predicted Log D Values for FC101 at Various pH's. Log D properties of FC101 were predicted using ACD/labs 11.0 software. Experimentally measured Log D was done by the shaken-flask method using n-octanol/phosphate buffer to determine the experimental ionized partition coefficient for FC101 (For details, see Methods). Note that while the two methods agree closely at pH 7.0-7.6, the partition coefficients diverge at either higher or lower pH values.

FIGS. 5A and 5B show FC101 uptake in MCF7 cells at 0 seconds and at 10 seconds, respectfully.

Figure 6:
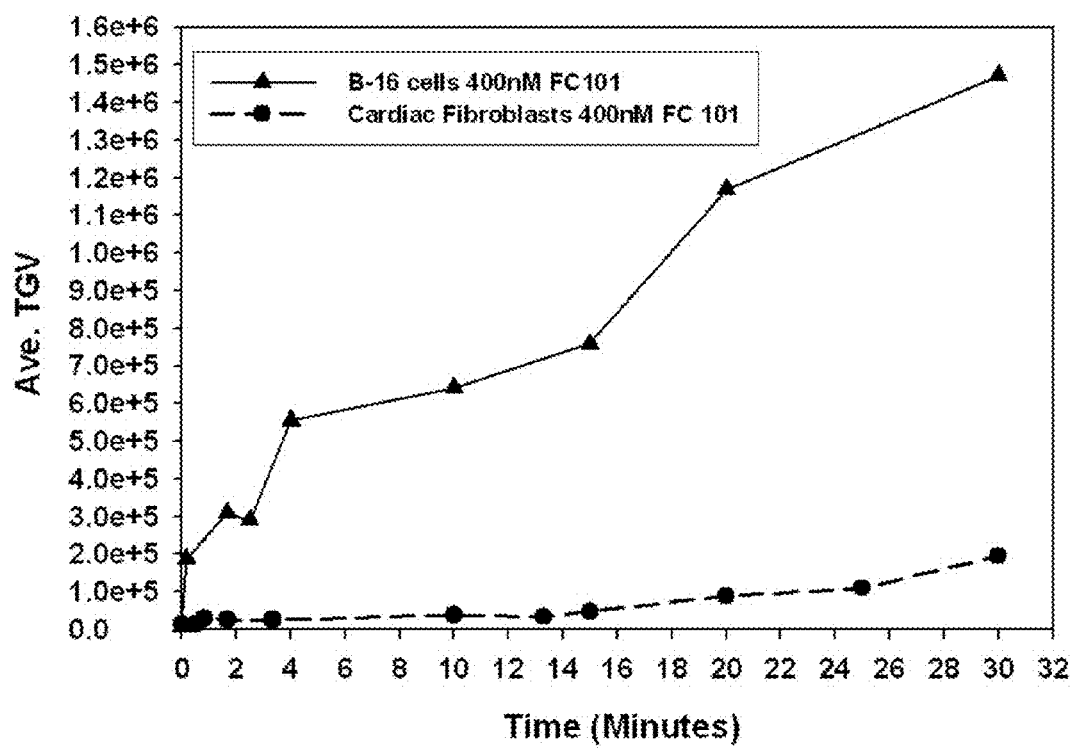

FIG. 6 is shown to scale comparison of cardiac and B16 cells.

FIG. 7 shows 500,000 cells/ml at various FC101 doses.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

In general, the present disclosure is directed to the use of FC101 in photodynamic therapy to treat cancer, skin diseases (e.g., eczema, psoriasis and vitiligo, and mycosis fungoides), and other diseases. The preparation and use of FC101 as a chemotherapeutic agent for the treatment of cancer and other angiogenic diseases is described in U.S. Pat. No. 7,078,433; U.S. Pat. No. 6,660,765; U.S. Pat. No. 6,225,340; and U.S. Pat. No. 5,932,611, all of which are hereby incorporated by reference in their entirety.

It has now been discovered that FC101 is also effective as a photosensitizing agent in the treatment of cancer and other diseases. Thus, treatment of cancerous cells with access to treatment by an energy source (e.g., UV light) can be improved while other cancerous cells in the body not accessible to an energy source can still be treated via FC101's chemotherapeutic properties. This treatment method can, therefore, accelerate the therapy process for those diseases where the diseased cells are accessible to a light source, while simultaneously treating other diseased areas. For example, PTD utilizing FC101 can be used to treat cancerous cells found in the skin, colon, lungs, mouth/throat, and other accessible areas on the human body. Other cancerous cells in non-accessible areas of the body can also be treated simultaneously with FC101, without the use of the energy source, since FC101 is a chemotherapeutic agent.

The present invention also generally describes the uptake kinetics and cellular disruption of a unique drug, FC101, which has both natural anti-tumorgenic properties and intrinsic fluorescence in blue light. Being a fluorescent compound, it was possible to monitor and describe the kinetics of the uptake of this drug into normal cells and transformed cells using time-lapse-fluorescence microscopy and describe the entry and localization of FC101 in normal and transformed cells.

I. FC101

The treatment of certain diseases in humans or in animals can be achieved by the present method of PDT, comprising the administration of a therapeutically active dosage of a water soluble compound isolated and purified from *Fusarium* fungal cultures followed by the application of light energy to the targeted cells. Specifically, the preferred mode employs administering FC101, derived from *Fusarium equiseti* cultures, as a treatment to selectively accumulate in diseased cells.

Treatment with FC101 can be administered in dosages and by techniques well known to those skilled in the medical or veterinary arts, taking into consideration such factors as the age, sex, weight, species and condition at the particular patient, and the route of administration. The route of administration can be percutaneous, via mucosal administration (e.g., oral, nasal, anal, vaginal) or via a parenteral route (intradermal, intramuscular, subcutaneous, intravenous, or intraperitoneal). FC101 can be administered alone, or can be coadministered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. FC101 may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "REMINGTON'S PHARMACEUTICAL SCIENCE," 17th edition, 1985, may be consulted to prepare suitable preparations, without undue experimentation.

As mentioned above, the effective dosage and route of administration are determined by the therapeutic range and nature of the compound, and by known factors, such as the age, weight, and condition of the host, as well as screening procedures which are known and do not require undue experimentation. Dosages can generally range from a few hundred milligrams to a few grams (e.g., in an amount of about 0.2 µg to about 200 g). Dosages can be administered in a series of treatment cycles over the treatment period.

The chemical structure of FC101 (5-amino-2,2-dimethyl-6-[3'-(R,S)amino-4'-hydroxy-butan-1-one]-2,3-dihydro-4H-1-benzopyran-4-one) has previously been determined. The general structure can be shown in Formula I:

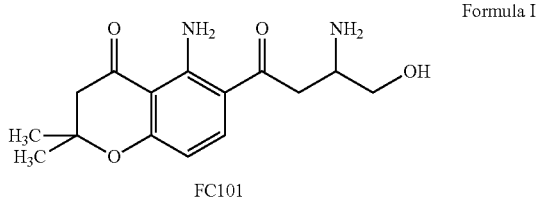 [SMILES: CC1(C)CC(=O)c2c(ccc(C(=O)CC(N)CO)c2N)O1 ; "FC101"]

Formula I

FC101

As shown, alternating carbonyl and amino groups appear on the upper face of this largely planar chromanone, with a terminal primary alcohol on the side chain, as well as a gem-dimethyl group adjacent to the ring-O. The anilinic amine is not titratable due to H-bonding between the adjacent carbonyl groups. The R-amino group on C-3 of the side chain has a pKa of 8.6 and is the only chiral center in the molecule.

In accordance with standard methods well known to those skilled in the art, FC101 can be used as a lead compound to create analog compounds. Analog compounds possess similar biological functions, but differ in their chemical structure. Such compounds may be created by substituting different functional groups, such as methyl, acetyl, amino or hydroxyl groups, for those already present on the parent compound or the analog compounds have a methyl, acetyl, amino, or hydroxyl group at a position which is unsubstituted in 5-amino-2,2-dimethyl-6-[3'-(R,S)amino-4'-hydroxy-butan-1-one]-2,3-dihydro-4H-1-benzopyran-4-one. Additional functional groups may also be added to the parent FC101. The resulting compounds may exhibit more desirable therapeutic properties, or be more pharmacologically active, than the parent molecule, FC101. Standard texts, such as "PRINCIPLES OF MEDICINAL CHEMISTRY," William O. Foye, Thomas L. Lemke, and David A. Williams, editors, 4th ed., 1995, may be consulted to produce such compounds, without undue experimentation.

II. Accumulation of FC101 in Diseased Cells

Through the use of confocal microscopy, the kinetic uptake and accumulation of fusarochromanone (FC101) was determined in both living tumorigenic and normal cells. Like other fluorescent cationic molecules, FC101 showed increased accumulation in tumorigenic cells; however, unlike other molecules, it appeared to be accumulated in a time dependent manner. Also, unlike traditional fluorescent molecules, FC101 a potent inhibitor of cell growth, showed preferential inhibition of tumorigenic B-16 melanoma cells when compared to normal cardiac fibroblasts. Further analysis of FC101's physicochemical properties using both experimentally obtained and simulated values revealed the likelihood of membrane permeation and oral bioavailability of the compound. These physicochemical properties of FC101 were also used to predict its intracellular localization lending credence to data observed by confocal microscopy.

In the diseased cells, FC101 maximally concentrates in the perinuclear cytoplasm, associating with the lysosomes, endoplasmic reticulum and Golgi organelles. In particular, it is believed that FC101 tends to localize in the lysosomal granules. Then, upon excitation by light energy, FC101 emits fluorescence in its energetic state. In the energetic state, FC101 functions to form reactive oxygen species or act as a free radical. The activated FC101 or oxygen species localized in lysosome destroys the lysosome releasing lysosomal enzymes which in turn destroy the transformed cells.

III. Light Energy Treatment

Once FC101 has accumulated in the diseased cells, any areas accessible to light energy treatment can be illuminated. It is believed that the application of light energy excites electrons in the FC101 molecule leading to the production of free radicals, especially in the presence of oxygen. Free radical molecules are generally atoms, molecules or ions with highly reactive electrons (sometimes unpaired electrons), such as $H_2O_2$, $O_2^-$, NO, $^-OH$, and the like. Once formed in the cell, these free radicals can kill the diseased cells. Thus, the light energy treatment can accelerate the treatment and recovery process than chemotherapy using FC101 without any application of light energy. Also, the light energy treatment can be focused on those diseased cells to cause as little harm as possible to other healthy cells.

The light energy is generally applied from a light source producing the desired wavelength of light. In most embodiments, the light energy used is ultraviolet ("UV") light, which is electromagnetic radiation with a wavelength shorter than that of visible light, but longer than x-rays, in the range of about 10 nm to about 400 nm, and energies from 3 eV to 124 eV. In one particular embodiment the UV light used has a wavelength of from about 300 nm to about 400 nm, such as from about 350 nm to about 400 nm, and such as about 365 nm to about 385 nm. However, other wavelengths of light energy (e.g., blue-violet light having a wavelength of about 380 nm to about 465 nm) may be utilized.

The targeted cells can be illuminated with the light energy for any desired time determined according to the treatment guidelines. Generally, the treatment process can involve repeated exposure to light energy for short intervals of time (e.g., from about 2 minutes to about 10 minutes); however, any period of exposure can be utilized according to particular treatment plan prescribed by the attending physician(s).

The light source can be any of the commercially available light sources, which are commonly available having a light source of about 365 nm.

The following examples are meant to be exemplary procedures only which aid in the understanding of the present invention. The invention is not meant to be limited thereto.

Example 1

Material and Methods

Cell Culture:

Mouse B-16 melanoma cells were grown to 60-70% confluence in T25 flasks (Corning) before use in confocal and inhibition studies. Growth medium for the B16 cells was RPMI (HyClone) supplemented with 10% FBS (Gibco), L-glutamine (2 mM), Hepes (25 mM), and penicillin/streptomycin/amphotericin (PSA, Gibco). Normal primary cultured rat cardiac fibroblasts were similarly grown to 60-70% confluence before use in confocal and inhibition studies, and served as non-transformed controls. Growth medium for the cardiac fibroblasts was in DMEM supplemented with 10% fetal bovine serum (FBS) and PSA (Gibco). For confocal studies both cell types were grown to 50-60% confluence in MatTek (MatTek, Corp. Ashland, Mass.) culture dishes and maintained in the same growth media listed above, respectively. For growth inhibition studies both cell types were grown in 96 well plates (Costar) and maintained in the same growth media listed above.

To study the timing of dose-response, the effect of FC101 on melanoma cell division was measured by [$^3$H]thymidine incorporation. Briefly, two human melanoma cell lines (Dréau et al, unpublished) were seeded at $10^4$ cells/well in 96-well plates and cultured in RPMI-1640 media supplemented with 10% FBS, antibiotics and amphotericin B, and incubated at 37° C. and 5% $CO_2$. After one day of culture, [$^3$H]thymidine (1 µCi/ml) and FC101 (0-800 nmol/liter) were added to the culture medium. After 1, 4, 8 and 12 days of incubation, cells were washed 3× with phosphate buffered saline (PBS) to remove unincorporated label and the amount of incorporated [$^3$H]thymidine was measured using scintillation counting (Packard Instruments, Meriden, Conn., USA). [$^3$H]thymidine incorporation was expressed as counts per minute (cpm) per culture well.

Reagents:

FC101 was isolated and purified from *Fusarium equiseti* grown on rice cultures {Wuthier Unpublished}. FC101 was then recrystallized to form the more stable phosphate salt form (MW 390.3). Its purity (>99%) was confirmed by $H^1$-NMR, TLC, and UV-Vis spectroscopy.

MTT (3-(4,5-Dimethylthiazol-2-yl)-2,5-diphenyltetrazolium bromide), DMSO (dimethyl sulfoxide), n-octanol, sodium phosphate dibasic, Hanks Balanced Salt buffer (HBS), Krebs-Henseleit Buffer (KHB), as well as all culture-related chemicals, were obtained from Sigma-Aldrich Chemicals (St. Louis, Mo.).

Determination of Cell Viability by MTT Assay

Cells were plated in a 96 well format containing 100 µl per well of appropriate media at a density of $2.5 \times 10^4$ cells/ml, and incubated at 37° C. with 5% $CO_2$. After a 24 h attachment period, the cells were treated in sextuplicate with 100 µl per well of varying concentrations (0 to 10 µM) of FC101. Final volume in each well was 200 µl. Cell proliferation was then determined by the MTT assay after 48 hr incubation period[8]. Briefly, 20 µl of a 5 mg/ml solution of MTT (dissolved in HBS) was added to each well. After 4.5 hr incubation at 37° C., the media were then removed and the insoluble mitochondrial-converted dye was solubilized in 100 µl of DMSO. The plates were placed on a shaker for 30 min to ensure that all of the dye was in solution and then read on a (Spectra Max plus 384, Molecular Devices) microplate reader at 570 and 640 nM. The background absorbency at 640 nM was subtracted from the 570 nM value before calculating the $GI_{50}$.

Calculated Physicochemical Properties of FC101

Physicochemical properties of FC101 were predicted using ACD/Log D Sol Suite 11.0 software (Advanced Chemistry Development). Basic prediction algorithms according to ACD/labs were used in the computational determination of log P and D are as follows: Log P=Σfn+ΣFm, and Log D=f (Log P, pKa)[9].

Experimental Log D for FC101

The shaken-flask method with n-octanol/phosphate buffer was used to determine the experimental ionized partition coefficient for FC101[10]. Briefly, 50 ml each of n-octanol and 0.1 M phosphate buffer (at appropriate pH) were added to a 125 ml flask and placed on a mechanical shaker at room temperature for 24 hours to ensure saturation of each phase. The phases were then separated by centrifugation (Damon IEC HN-SII) at 2000 rpm for 30 min. After separation, aliquots (1 ml) were taken from each phase and were placed in separate vials. A small sample (45.5 µl) of a stock solution of 10 mM FC101 in water was added to the aqueous phase. The phases were then combined (1 ml of each) for a final FC101 concentration of 65 µM and shaken for 30 mins (Spex Certiprep 8000 mixer), and then centrifuged (Eppendorf 5416) at 1500×g for 30 min to effect complete phase separation. The n-octanol was separated from the phosphate buffer and the absorbance at 385 nm (Shimadzu UV 1601) was then used to determine the concentration of FC101 in each phase. The partition coefficient was calculated using the following equation:

$$\text{Log}_{10} D = ([FC101_{charged+uncharged}]_{oct} / [FC101_{charged+uncharged}]_{buf})$$

Experimental Log P for FC101

The shaken-flask method was also used to determine the experimental non-ionized partition coefficient for FC101. The same procedure used in the experimental determination of Log D for FC101 was used to determine the Log P with the exception that double-distilled water adjusted to pH 10 with 1 mM NaOH was used instead of the phosphate buffer. The log P was calculated using:

$$\text{Log}_{10} P = \text{Log}_{10}([FC101_{uncharged}]_{oct} / [FC101_{uncharged}]_{wat})$$

Imaging of Drug Uptake:

Cells growing in the Matra-Tek dishes were maintained in an environmental chamber (37° C. and 5% $CO_2$ atmosphere) mounted on the stage of a Zeiss inverted fluorescence microscope equipped with a CARV spinning disk confocal attachment. B16 cells were imaged using a Zeiss 63× oil NA=1.4 apochromatic objective, which gave an image field of 7265.15 µm². Cardiac Fibroblasts were imaged using a Zeiss 40× oil 1.0 NA apochromatic objective, which gave an image field of 18,006.85 µm². The images were captured using a CCD camera (Hamamatsu ORCA-ER) controlled by Kinetic Imaging Image Acquisition Software (AQM Advance-6) software. All images were recorded at a constant exposure (385 ms) using a DAPI (360/460) filter set, which isolates the natural fluorescence of the compound.

The cells were maintained in 1 ml of tissue culture medium and allowed equilibrate in the environmental chamber, before imaging of the selected group of cells was initiated. Groups of B16 cells selected for measurements consisted of an average of 19.2±3.0 cells per field, with a total cellular area of 2050±156 µm². The groups of normal cardiac fibroblasts selected for measurements consisted of an average of 8.2±2.6 cells per field, with a total cellular area of 2716±185 μm². An appropriate volume of FC101 was added to the culture medium in the Matra-Tek dish to give the desired final concentration (50, 200, 400, 600, 800, 1000 nM) during continuous recording and image acquisition of the group of selected cells. The rate of entry of the drug into the cells was determined by high-speed image collection (1 sec interval, 60 exposures per min). The equilibrium-concentration uptake of the drug was determined by slow-speed time-lapse imaging (10 sec intervals, 6 exposures per min) collected for a minimum of 30 minutes. In all experiments, images were recorded prior to addition of the drug to provide a negative control of any auto-fluorescence present in the cells. In some samples, imaging was continued at 10 minute intervals up to 60 minutes.

Measurement of Drug Uptake by Image Analysis:

FC101 is a naturally fluorescent molecule and its movements, accumulation and distribution within living cells can be followed and analyzed in real-time or by time-lapse imaging. Cellular uptake of the drug was analyzed using the integrated morphometry subroutine of MetaMorph 6.1 (MDS Analytical Technologies). Briefly, the original color images were converted to 16-bit monochrome images. The drug fluorescence in the cytoplasm of the cells was thresholded as a region of interest and the integrated optical density (IOD) of the drug fluorescence was measured for all cells in the field at each time point. Values of image brightness, contrast and gamma function were kept constant for all image measurements of drug fluorescence.

Descriptors of the Change in Drug Fluorescence in the Cytoplasm:

The IOD of the natural fluorescence of the drug was measured and used as the descriptor of drug uptake in the cell, using the imaging software for each thresholded and isolated cellular region expressing drug fluorescence. The IOD of the region of fluorescence delineated by the thresholded boundaries was considered to be the "mass" of FC101 concentrated within that region and a measurement proportional to the total amount of fluorescent material (FC101 concentration) in the thresholded region[11-14]. The IOD can be defined as the weighted sum of the image histogram in which each term in the histogram was multiplied by the gray value it represents. When applied to thresholded boundaries, the IOD can be expressed as:

$$IOD(T_1, T_2) = \sum_{GV = T_1}^{T_2} H(GV) \times GV$$

where $T_1$ and $T_2$ represent the upper and lower thresholds defining the region of interest in the histogram, GV is the gray value of each pixel, and H(GV) is the gray level histogram. Values of IOD were calculated directly from the integrated morphometry subroutine of MetaMorph image analysis software. Using the software's optical calipers, the measurements were refined by setting specific boundary conditions for acceptance of the IOD measurement of fluorescent signal from the labeled cells and to minimize or eliminate the contributions of any nonspecific and background auto-fluorescence. In these images the non-cellular background fluorescence of the FC101 in the medium was minimal in comparison to the fluorescence signal from intracellular FC101.

Results

The most striking observation is that FC101 enters tumorgenic B16 cells within 3 seconds following addition of the compound to the medium in contact with the cells. The membrane of the tumorgenic cells appears to offer little or no resistance to entry of FC101, which rapidly accumulates in these cells, reaching a steady-state maximum within 1 to 2 minutes following addition of the compound. The B16 melanoma cells first pull in the filopodia, and then the membranes begin blebbing. Finally, the cells lysed and the sequestered fluorescence is released. The magnitude of the steady-state maximum in response to different concentrations of FC101 is essentially linear for transformed cells and appears solely dependent on the external concentration of the FC101. It is speculated that the rapid accumulation of FC101 into the B16 melanoma cells may be due to their more acidic intracellular pH compared to that of normal fibroblasts. This difference in intracellular pH is due the higher rate of aerobic glycolysis and hypoxic conditions found in tumor cells[9].

In remarkable contrast, entry of FC101 in normal, primary cardiac fibroblasts was slow, requiring between three to four minutes, followed by a stable, steady equilibrium which required between 10 to 20 minutes to develop. In normal cells, the steady-state equilibrium concentration dose response of FC101 was non-linear, indicating a different mechanism of uptake. Thus, normal cells have a greater degree of control over the entry and accumulation of FC101 than do the tumorgenic cells.

Since FC101 is a small cationic molecule with moderate lipophilicity and processes inherit blue fluorescence, this molecule can be developed for use in the diagnosis of cancer and other applicable diseases. Although there is much evidence to show that small molecules enter by simple diffusion, FC101 shows differential properties, appearing to enter transformed cell by simple diffusion, but conversely to enter normal cells by some other process.

Interestingly, transformed cells loaded with FC101 undergo cell death as evidenced by the formation of large vacuoles in the presence of blue exposure during the collection of time lapse images. Since the cells are exposed to only small amounts, this indicates that FC101 kills tumor cells by a phototoxic effect. Normal cells do not exhibit this effect and their most notable response to FC101 is to undergo morphological changes in which the cells assume a more rounded morphology. This response is typical for fibroblasts responding to noxious stimulus and is considered a natural, survival, defense process.

A mechanism for the phototoxic effect of FC101 arises from its apparent localization in the lysosomal granules and its excitation by blue light to emit fluorescence. In the energetic state, FC101 functions to form reactive oxygen species or act as a free radical. The activated FC101 or oxygen species localized in lysosome destroys the lysosome releasing lysosomal enzymes which in turn destroy the transformed cells. Also, there is evidence of lipid oxidation occurring at the membrane surface. This can be seen due to the blebbing of the membrane surface.

This drug began to effectively kill B-16 cells as evidenced by the formation of multiple large fluid filled vacuoles. These vacuoles appeared in all cells following the addition of the drug. These vacuoles did not contain any detectable drug fluorescence and were devoid of cellular organelles. These observations indicate that the drug compromises membrane integrity allowing fluid to enter the cell resulting in a hypo-osmotic state.

The ineffectiveness of the FC101 to kill normal cells indicates that normal cells have the capacity to scavenge the free radicals generated by the interaction of FC101 and blue light.

Example 2

Material and Methods

Cell Culture:

Mouse B-16 melanoma cells were grown to 60-70% confluence in T25 flasks (Corning) before use in confocal and inhibition studies. Growth medium for the B16 cells was RPMI (HyClone) supplemented with 10% FBS (Gibco), L-glutamine (2 mM), Hepes (25 mM), and penicillin/streptomycin/amphotericin (PSA, Gibco). Normal primary cultured rat cardiac fibroblasts were similarly grown to 60-70% confluence before use in confocal and inhibition studies, and served as non-transformed controls. Growth medium for the cardiac fibroblasts was in DMEM supplemented with 10% fetal bovine serum (FBS) and PSA (Gibco). For confocal studies both cell types were grown to 50-60% confluence in MatTek (MatTek, Corp. Ashland, Mass.) culture dishes and maintained in the same growth media listed above, respectively. For growth inhibition studies both cell types were grown in 96 well plates (Costar) and maintained in the same growth media listed above.

To study the timing of dose-response, the effect of FC101 on melanoma cell division was measured by [$^3$H]thymidine incorporation. Briefly, two human melanoma cell lines (Dréau et al, unpublished) were seeded at $10^4$ cells/well in 96-well plates and cultured in RPMI-1640 media supplemented with 10% FBS, antibiotics and amphotericin B, and incubated at 37° C. and 5% $CO_2$. After one day of culture, [$^3$H]thymidine (1 µCi/ml) and FC101 (0-800 nmol/liter) were added to the culture medium. After 1, 4, 8 and 12 days of incubation, cells were washed 3× with phosphate buffered saline (PBS) to remove unincorporated label and the amount of incorporated [$^3$H]thymidine was measured using scintillation counting (Packard Instruments, Meriden, Conn., USA). [$^3$H]thymidine incorporation was expressed as counts per minute (cpm) per culture well.

Reagents:

FC101 was isolated and purified from *Fusarium equiseti* grown on rice cultures {Wuthier Unpublished}. FC101 was then recrystallized to form the more stable phosphate salt form (MW 390.3). Its purity (>99%) was confirmed by $H^1$-NMR, TLC, and UV-Vis spectroscopy.

MTT (3-(4,5-Dimethylthiazol-2-yl)-2,5-diphenyltetrazolium bromide), DMSO (dimethyl sulfoxide), n-octanol, sodium phosphate dibasic, Hanks Balanced Salt buffer (HBS), Krebs-Henseleit Buffer (KHB), as well as all culture-related chemicals, were obtained from Sigma-Aldrich Chemicals (St. Louis, Mo.).

Determination of Cell Viability by MTT Assay

Cells were plated in a 96 well format containing 100 µl per well of appropriate media at a density of $2.5 \times 10^4$ cells/ml, and incubated at 37° C. with 5% $CO_2$. After a 24 h attachment period, the cells were treated in sextuplicate with 100 µl per well of varying concentrations (0 to 10 µM) of FC101. Final volume in each well was 200 µl. Cell proliferation was then determined by the MTT assay after 48 hr incubation period[8]. Briefly, 20 µl of a 5 mg/ml solution of MTT (dissolved in HBS) was added to each well. After 4.5 hr incubation at 37° C., the media were then removed and the insoluble mitochondrial-converted dye was solubilized in 100 µl of DMSO. The plates were placed on a shaker for 30 min to ensure that all of the dye was in solution and then read on a (Spectra Max plus 384, Molecular Devices) microplate reader at 570 and 640 nM. The background absorbency at 640 nM was subtracted from the 570 nM value before calculating the $GI_{50}$.

Calculated Physicochemical Properties of FC101

Physicochemical properties of FC101 were predicted using ACD/Log D Sol Suite 11.0 software (Advanced Chemistry Development). Basic prediction algorithms according to ACD/labs were used in the computational determination of log P and D are as follows: Log P=$\Sigma$fn+$\Sigma$Fm, and Log D=f (Log P, pKa)[9].

Experimental Log D for FC101

The shaken-flask method with n-octanol/phosphate buffer was used to determine the experimental ionized partition coefficient for FC101[10]. Briefly, 50 ml each of n-octanol and 0.1 M phosphate buffer (at appropriate pH) were added to a 125 ml flask and placed on a mechanical shaker at room temperature for 24 hours to ensure saturation of each phase. The phases were then separated by centrifugation (Damon IEC HN-SII) at 2000 rpm for 30 min. After separation, aliquots (1 ml) were taken from each phase and were placed in separate vials. A small sample (45.5 µl) of a stock solution of 10 mM FC101 in water was added to the aqueous phase. The phases were then combined (1 ml of each) for a final FC101 concentration of 65 µM and shaken for 30 mins (Spex Certiprep 8000 mixer), and then centrifuged (Eppendorf 5416) at 1500×g for 30 min to effect complete phase separation. The n-octanol was separated from the phosphate buffer and the absorbance at 385 nm (Shimadzu UV 1601) was then used to determine the concentration of FC101 in each phase. The partition coefficient was calculated using the following equation:

$$\text{Log}_{10}D = ([FC101_{charged+uncharged}]_{oct} / [FC101_{charged+uncharged}]_{buf})$$

Experimental Log P for FC101

The shaken-flask method was also used to determine the experimental non-ionized partition coefficient for FC101. The same procedure used in the experimental determination of Log D for FC101 was used to determine the Log P with the exception that double-distilled water adjusted to pH 10 with 1 mM NaOH was used instead of the phosphate buffer. The log P was calculated using:

$$\text{Log}_{10}P = \text{Log}_{10}([FC101_{uncharged}]_{oct} / [FC101_{uncharged}]_{wat})$$

Imaging of Drug Uptake:

Cells growing in the Matra-Tek dishes were maintained in an environmental chamber (37° C. and 5% $CO_2$ atmosphere) mounted on the stage of a Zeiss inverted fluorescence microscope equipped with a CARV spinning disk confocal attachment. B16 cells were imaged using a Zeiss 63× oil NA=1.4 apochromatic objective, which gave an image field of 7265.15 µm². Cardiac Fibroblasts were imaged using a Zeiss 40× oil 1.0 NA apochromatic objective, which gave an image field of 18,006.85 µm². The images were captured using a CCD camera (Hamamatsu ORCA-ER) controlled by Kinetic Imaging Image Acquisition Software (AQM Advance-6) software. All images were recorded at a constant exposure (385 ms) using a DAPI (360/460) filter set, which isolates the natural fluorescence of the compound.

The cells were maintained in 1 ml of tissue culture medium and allowed equilibrate in the environmental chamber, before imaging of the selected group of cells was initiated. Groups of B16 cells selected for measurements consisted of an average of 19.2±3.0 cells per field, with a total cellular area of 2050±156 µm². The groups of normal cardiac fibroblasts selected for measurements consisted of an average of 8.2±2.6 cells per field, with a total cellular area of 2716±185 µm². An appropriate volume of FC101 was added to the culture medium in the Matra-Tek dish to give the desired final concentration (50, 200, 400, 600, 800, 1000 nM) during continuous recording and image acquisition of the group of selected cells. The rate of entry of the drug into the cells was determined by high-speed image collection (1 sec interval, 60 exposures per min). The equilibrium-concentration uptake of the drug was determined by slow-speed time-lapse imaging (10 sec intervals, 6 exposures per min) collected for a minimum of 30 minutes. In all experiments, images were recorded prior to addition of the drug to provide a negative control of any auto-fluorescence present in the cells. In some samples, imaging was continued at 10 minute intervals up to 60 minutes.

Measurement of Drug Uptake by Image Analysis:

FC101 is a naturally fluorescent molecule and its movements, accumulation and distribution within living cells can be followed and analyzed in real-time or by time-lapse imaging. Cellular uptake of the drug was analyzed using the integrated morphometry subroutine of MetaMorph 6.1 (MDS Analytical Technologies). Briefly, the original color images were converted to 16-bit monochrome images. The drug fluorescence in the cytoplasm of the cells was thresholded as a region of interest and the integrated optical density (IOD) of the drug fluorescence was measured for all cells in the field at each time point. Values of image brightness, contrast and gamma function were kept constant for all image measurements of drug fluorescence.

Descriptors of the Change in Drug Fluorescence in the Cytoplasm:

The IOD of the natural fluorescence of the drug was measured and used as the descriptor of drug uptake in the cell, using the imaging software for each thresholded and isolated cellular region expressing drug fluorescence. The IOD of the region of fluorescence delineated by the thresholded boundaries was considered to be the "mass" of FC101 concentrated within that region and a measurement proportional to the total amount of fluorescent material (FC101 concentration) in the thresholded region[11-14]. The IOD can be defined as the weighted sum of the image histogram in which each term in the histogram was multiplied by the gray value it represents. When applied to thresholded boundaries, the IOD can be expressed as:

$$IOD(T_1, T_2) = \sum_{GV=T_1}^{T_2} H(GV) \times GV$$

where $T_1$ and $T_2$ represent the upper and lower thresholds defining the region of interest in the histogram, GV is the gray value of each pixel, and H(GV) is the gray level histogram. Values of IOD were calculated directly from the integrated morphometry subroutine of MetaMorph image analysis software. Using the software's optical calipers, the measurements were refined by setting specific boundary conditions for acceptance of the IOD measurement of fluorescent signal from the labeled cells and to minimize or eliminate the contributions of any nonspecific and background auto-fluorescence. In these images the non-cellular background fluorescence of the FC101 in the medium was minimal in comparison to the fluorescence signal from intracellular FC101.

Results

Inherent Fluorescence Characteristics of Normal Cardiac Fibroblasts, and B-16 Melanoma Cells Normal cardiac fibroblasts exhibit a characteristic array of auto-fluorescence granules predominately localized in the perinuclear cytoplasm, but also present in the peripheral and marginal cytoplasm. The auto-fluorescence of these granules in cardiac fibroblasts is highly variable (FIG. 2E) and expressed a mean total IOD=341±116. The auto-fluorescence present in cardiac fibroblasts appears very stable over time (FIG. 6E, 0 nM).

The B-16 melanoma cells (FIG. 2A) are also characterized by a concentration of weak auto fluorescent cytoplasmic granules with a mean total IOD=280±129, which was comparable to that seen in the normal cardiac fibroblasts. These granules are predominantly localized in the perinuclear cytoplasm with a few granules being scattered in the peripheral and marginal cytoplasm. The auto-fluorescence of these cytoplasmic granules in the B16 cells also appears stable, expressing minimal photo bleaching (FIG. 2A, 0 nM).

Cellular Incorporation of FC101—Uptake of FC101 by B-16 Melanoma Cells

At all concentrations studied, the incorporation of FC101 by the B-16 melanoma cells was rapid. Upon addition of the FC101 to the medium, there was a rapid increase in overall fluorescence in the medium and cells. This initial increase was followed by an immediate decline in overall fluorescence as the drug diffused throughout the medium. A dramatic and distinct change in the intensity of the intracellular fluorescence in the B-16 cells appeared within 3 seconds following addition of the drug (FIG. 2B). This rapid and significant increase of intracellular fluorescence over intracellular auto-fluorescence indicated that FC101 was capable of freely diffusing across the plasma membrane to enter the cell. Following the initial rapid increase in intracellular drug concentration, a steady state of FC101 concentration in the perinuclear cytoplasm was established within 1 to 2 minutes (FIG. 2C). The IOD of the FC101 fluorescence remained relatively constant for the duration of the experiment out to 20 or 60 minutes (FIG. 2D).

The intracellular accumulation of the FC101 was predominantly localized in the perinuclear cytoplasm. This localization appeared asymmetrical, with the highest concentration apparently localized in the perinuclear endoplasmic reticulum, and Golgi apparatus. Localization of FC101 in the perinuclear region was stable and exhibited minimal photobleaching. The non-bound FC101 in the medium, which was not internalized by the cells, underwent rapid photobleaching. The magnitude of the intracellular steady-state concentration measured for drug uptake in B-16 cells was dependent on the initial concentration of FC101 added to medium (FIG. 3A).

Dose-Response Uptake of FC101 in B-16 Melanoma Cells

With increasing concentrations of FC101 added to the medium, the steady-state fluorescence IOD of FC101 localized to the perinuclear cytoplasm was proportionally higher. The rate of FC101 entry into the B-16 cells was rapid (2-3 seconds) at all concentrations. The mean equilibrium concentration values of the intracellular fluorescence (IOD) of FC101 were linearly correlated with the initial concentration of FC101 to which the cells were exposed ($R^2$=0.970; FIG. 3B). These observations indicate that the magnitude of FC101 accumulation in the perinuclear cytoplasm of the cells was dependent on initial extracellular concentration of FC101. Furthermore, the uptake of FC101 by B-16 cells is governed by first-order kinetics, and that FC101 moves into the cell by free diffusion—not requiring a carrier protein, specific channel or the expenditure of energy.

FC101 Uptake by Normal Cardiac Fibroblasts

In dramatic contrast, the uptake of FC101 by cardiac fibroblasts was very slow. No incorporation of FC101 was observed in less than a minute (FIG. 2F). Initial appearance of FC101 in the cytoplasm of cardiac fibroblasts required 3 to 4 minutes (FIG. 2G). Establishment of a steady-state equilibrium of FC101 in the cytoplasm of cardiac fibroblasts required between 10 to 15 minutes (FIG. 2H) for concentrations ranging between 50-400 nM. However, once the equilibrium concentration of FC101 was established, little further change in intracellular IOD was observed (FIG. 4A). Like in B-16 cells, in cardiac fibroblasts, FC101 was also predominantly localized to the perinuclear cytoplasm, but was also present in granules scattered in the peripheral and marginal cytoplasm (FIG. 2G). At higher concentrations>400 nM or longer incubation times (FIG. 2H), the fluorescence of FC101 saturated the cytoplasm making the measurements unreliable. This slow change was accompanied by an increase in IOD, suggesting re-arrangement or movement of FC101 already present in the cytoplasm (FIG. 4A, 400 nM).

Dose-Response Uptake of FC101 in Cardiac Fibroblasts

Cardiac fibroblasts also demonstrated a characteristic dose response which was different from that seen in the B-16 cells. Comparison of the mean equilibrium concentration values of the intracellular fluorescence (IOD) of FC101 with initial concentrations of FC101 to which the cells were exposed resulted in a non-linear exponential correlation (FIG. 4B; $R^2=0.996$ [ Note that the Y-axis is in exponential terms.]; both exponential). This indicates that in normal cardiac fibroblasts both the rate of FC101 uptake into the cell and magnitude of the final intracellular concentration are dependent on the initial external concentration of FC101. These observations further indicate that FC101 is not freely diffusible across the membrane in cardiac fibroblasts (normal cells) and its uptake is mediated by higher order kinetics than those seen in B-16 melanoma cells.

Predicted and Experimentally Observed Physiochemical Properties of FC101

Log P is defined as the partition of non-ionized molecules between n-octanol and water; it is used to determine the lipophilicity of a molecule. Computational calculation of Log P for FC101 yielded a value of 0.76, which was in fair agreement with the experimental value of 1.62 found using the shaken-flask method. The solution was adjusted to a pH of 10 to ensure that all the FC101 was in the non-ionized form.

Log D is defined as the partition of the ionized and non-ionized molecules in a biphasic mixture of n-octanol and aqueous buffer. Computational calculation of Log D for FC101 was also done using the ACD/labs software. Here, computational and experimental values were in close agreement with each other at physiological pH, but failed when the pH was either increased or decreased from physiological (FIG. 5). While obvious physiochemical parameters such as the number of rotatable bonds, MW, H-bond acceptors and donors are in exact agreement, comparison of other physiochemical parameters such as Log P, and pKa, predicted using the ACD software were close to experimentally found values (Table 1).

TABLE 1

Comparison of Experimental and Predicted Physicochemical Properties of FC101.

| FC101 Physicochemical Properties | $Log_{10}$ P | $Log_{10}$ $D_{7.6}$ | $pK_a$ | PSA | No. of Rotatable Bonds | MW | Hydrogen Bond Acceptors | Hydrogen Bond Donors |
|---|---|---|---|---|---|---|---|---|
| Experimental | 1.62 | 0.38 | 8.6 | NA | 7 | 292.3 | 6 | 5 |
| ACD Predicted | 0.76 | 0.30 | 6.96 | 115.64 | 7 | 292.3 | 6 | 5 |

FC101 maximally concentrates in the perinuclear cytoplasm, associating with the lysosomes, endoplasmic reticulum and Golgi organelles. This occurred in both the B16 melanoma and cardiac fibroblasts. Concentration of fluorescent compounds in specific organelles has been associated with the physiochemical properties of a small molecule. The localization of FC101 in the endoplasmic reticulum and Golgi apparatus is in agreement with other fluorescent compounds that have log P's between 0 to 5[15, 16]. Another physical property that has been linked to organelle accumulation is pKa. With FC101 having a pKa of 8.6 and the appearance of fluorescent granules, is indicative of FC101 accumulating the in the lysosomes of both cell types. Lysosomal accumulation has also been described in molecules with pKa's between 7.4 and 9.0[15]. The accumulation of weakly basic molecules in the acidic compartment of lysosomes is well documented and it is not surprising that FC101 falls into this category as well[17,18]. The concentration of FC101 in these localized areas may provide insights into the drug's mode of action.

Membrane permeability and oral bioavailability have been attributed to physical properties such as lipophilicity, molecular flexibility, polar surface area (PSA), and hydrogen bonding. Being able to use these physical factors to predict drug permeation and absorption in silico has been a long-standing goal. Typically these programs work well with structurally similar molecules, but fail when increased structural diversity is introduced[19]. Understanding-how natural small molecules permeate a cell membrane, and identifying its physical characteristics, may aid in improving the accuracy of computational programs. As shown in Table 1, the calculated and experimentally determined physical attributes of FC101 meet the criteria laid out by Lipinski and Veber for small molecules capable of membrane permeation and intestinal absorption[20, 21].

It was observed that FC101 enters the B16 melanoma cells within 3 seconds following addition of the compound to the medium in contact with the cells. The membrane of the tumorigenic cells appears to offer little or no resistance to entry of FC101, which rapidly accumulates in these cells, reaching a steady-state maximum within 1 to 2 minutes following addition of the compound. It is generally accepted that small nonpolar molecules can pass through the plasma membrane of a cell by simple diffusion[22]. Evidence for this has been described in the uptake of Adriamycin, quinidine, and rhodamine 123 in unilamellar and transbilayer vesicles[23, 24]. Simple diffusion has also been used to describe the uptake of doxorubicin, daunomycin, and rhodamine 123 in cultured transformed and normal cells[25-27]. The magnitude of the steady-state maximum in response to different concentrations of FC101 is essentially linear for transformed cells and appears solely dependent on the external concentration of the drug. The rapid accumulation of FC101 into the B16 melanoma cells can be due to their more acidic intracellular pH compared to that of normal fibroblasts. The uptake of weakly basic molecules has been attributed to some tumorigenic cells, which have lower intracellular pH's than are found in normal cells[26]. This difference in intracellular pH is due to the higher rate of aerobic glycolysis and hypoxic conditions found in tumor cells[28].

In remarkable contrast, entry of FC101 into normal, primary cardiac fibroblasts was slow, requiring between three to four minutes, followed by a stable, steady equilibrium which required between 10 to 15 minutes to develop. In normal cells, the steady-state equilibrium concentration dose-response of FC101 was non-linear, suggesting a different mechanism of uptake. Thus, normal cells have a greater degree of control over the entry and accumulation of FC101 than do the tumorigenic cells. Although there is much evidence to show that most small molecules enter cells by simple diffusion, FC101 shows differential properties, entering transformed cells by simple diffusion, but conversely entering normal cells by some other process. A difference in intracellular pH explains the change in uptake rate.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

REFERENCES

1. Walser, M. M.; Allen, N. K.; Mirocha, C. J.; Hanlon, G. F.; Newman, J. A., *Fusarium*-induced osteochondrosis (tibial dyschondroplasia) in chickens. *Vet. Pathol.* 1982, 19, (5), 544.
2. Lee, Y.-W.; Mirocha, C. J.; Shroeder, D.; Walser, M., TDP-1, a toxic component causing tibial dyschondroplasia in broiler chickens, and trichothecenes from *Fusarium roseum, Graminerarum. Appl Environ Microbiol* 1985, 50, (1), 15.
3. Xie, W. P.; Mirocha, C. J.; Pawlosky, R. J.; Wen, Y. C.; Xu, X. G., Biosynthesis of fusarochromanone and its monoacetyl derivative by *Fusarium equiseti. Appl. Environ. Microbiol.* 1989, 55, (4), 794.
4. Allen, N. K.; Jevne, R. L.; Mirocha, C. J.; Lee, Y. W., The Effect of a *Fusarium roseum* Culture and Diacetoxyscirpenol on Reproduction of White Leghorn Females. *Poul. Sci.* 1982, 61, 2172-2175
5. Minervini, F.; Lucivero, G.; Visconti, A.; Bottalico, C., Immunomodulatory effects of Fusarochromanones TDP-1 and TDP-2. *Natural Toxins* 1992, 1, (15).
6. Nie, D. Effects of fusarochromanone on endothelial cells: Implications in deficient vascularization in the pathogenesis of avian tibial dyschondroplasia. Ph.D Thesis, Univ. of South Carolina, Columbia, 1997.
7. Dréau, D.; Foster, M.; Hogg, M.; Culberson, C.; Nunes, P.; Wuthier, R. E., Inhibitory effects of fusarochromanone on melanoma growth. *Anti-Cancer Drugs* 2007, 18, (8), 897-904.
8. Sato, T.; Hashizume, M.; Hotta, Y.; Okahata, Y., Morphology and proliferation of B16 melanoma cells in the presence of lanthanoid and $Al^{3+}$ ions. *BioMetals* 1998, 11, 107-112.
9. ACD/PhysChem Predictor, version 11.00, Advanced Chemistry Development, Inc., Toronto ON, Canada, www.acdlabs.com, 2007.
10. OECD. OECD Guideline for Testing of Chemicals. Paris, 1987
11. Fuseler, J. W.; Millette, C. F.; Davis, J. M.; Wayne Carver, W., Fractal and image analysis of morphological changes in the actin cytoskeleton of neonatal caradaic fibroblasts in response to mechanical stretch. *Microsc. Microanal.* 2007, 13, 128-132.
12. Fuseler, J. W.; Merrill, D. W.; Grisham, M. B.; Wolf, R. E., Analysis and quantitation of NF-kB nuclear translocation in tumor necrosis factor alpha activated vascular endothelial cells. *Microsc. Microanal.* 2006, 12, 269-276.
13. Rogers, J. A.; Fuseler, J. W., Regulation of NF-kB activation and nuclear translocation by exogenous nitric oxide (NO) donors in the THF-á activated vascular endothelial cells. *Nitric Oxide* 2007, 16, 379-391.
14. Walter, J. R. J.; Berns, M. W., *Digital Image Processing and Analysis. In Video Microscopy*. New York and London: Plenum Press: 1986; p 327-392.
15. Horobin, R. W.; Stockert, J. C.; Rashid-Doubell, F., Fluorescent cationic probes for nuclei of living cells: why are they selective? A quantitative structure-activity relations analysis. *Histochem Cell Biol* 2006, 126, 165-175.
16. Rashid-Doubell, F.; Horobin, R. W., Selection of Fluorescent Golgi Complex Probes Using Structure-Activity Relationship Models. In *Biotechnology Applications of Microinjection, Microscopic Imaging, and Fluorescence*, al., P. H. B. e., Ed. Plenum Press: 1993.
17. Bulychev, A.; Trouet, A., Uptake and intracellular distribution of neutral red in cultured fibroblasts. *Exp. Cell. Res.* 1978, 115, 343-355
18. Yang, W. C.; Stasser, F. F., Mechanism of drug-induced vacuolization in tissue culture. *Exp. Cell. Res.* 1965, 38, 495-506.
19. Kramer, S. D., Absorption prediction from physicochemical parameters. *Pharma. Sci. & Tech. Today* 1999, 2, (9).
20. Lipinski, C. A.; Lombardo, F.; Dominy, B. W.; Feeney, P. J., Experimental and Computational approaches to estimate solubility and permeability in drug discovery and development settings. *Adv. Drug Delivery Rev.* 2001, 46, 3-26.
21. Veber, D. F.; Johnson, S. R.; Cheng, H.-Y.; Smith, B. R.; Ward, K. W.; Kopple, K. D., Molecular Properties That Influence the Oral Bioavailbility of Drug Candidates. *J. Med. Chem.* 2002, 45, 2615-2623.
22. Vattulainen, I., Molecules Dancing in Membranes. *Diffusion-Fundamentals* 2005, 2, (113.1-113.15).
23. L. D. Mayer, M. B. B., P. R. Cullis, Uptake of adiamycin into large unilamellar vesicles in response to p pH gradient. *Biochimica et Biophysica Acta-Biomembranes* 2003, 857, (1), 123-126.
24. Eytan, G. D.; Regev, R.; Oren, G.; Assaraf, Y. G., The Role of Passive Transbilayer Drug Movement in Multidrug Resistance and Its Modulation. *J. Biol. Chem.* 1996, 271, (22), 12897-12902.
25. Altenburg, G. A.; Vanoye, C. G.; Horton, J. K.; Reuss, L., Unidirectional fluxes of rhodamine 123 in multidrug-resistant cells: Evidence against direct drug extrusion from the plasma membrane. *Proc. Natl. Acad. Sci.* 1994, 91, 4654-4657.

26. Simon, S.; Roy, D.; Schindler, M., Intracellular pH and the control of multidrug resistance. *Proc. Natl. Acad. Sci.* 1994, 91, (1128-1132).
27. Spoelstra, E. C.; Westerhoff, H. V.; Dekker, H.; Lankelma, J., Kinetics of daunorubicin transport by P-glycoprotein of intact cancer cells. *Eur. J. Biochem.* 1992, 207, 567-579.
28. Warburg, O., On the Orgin of Cancer Cells. *Science* 1956, 123, (3191), 309-314.
29. Seidler, J.; McGovern, S. L.; Doman, T. N.; Shoichet, B. K., Identification and Prediction of Promiscuous Aggregating Inhibitors among Known Drugs. *J. Med. Chem.* 2003, 46, 4477-4486.
30. Testa, B.; Caldwell, J., Prodrugs Revisited: The "Ad Hoc" Approach as a Complement to Ligand Design. *Med. Res. Rev* 1996, 16, (3), 233-241.
31. Palm, K.; Stenberg, P.; Luthman, K.; Artursson, P.; Polar Molecular Surface Properties Predict the Intestinal Absorption of Drugs in Humans. *Pharma. Res.* 1997, 14, (5), 568-571
32. Bemporad, D.; Luttmann, C.; J. W. Essex, Computer Simulation of Small Molecule Permeation across a Lipid Bilayer: Dependence on Bilayer Properties and Solute Volume, Size, and Cross-Sectional Area. *Biophys. J.* 2004, 87, 1-13.

What is claimed:

1. A method of photodynamic therapy to treat a skin disease in an animal in need thereof, comprising:
   administering 5-amino-2,2-dimethyl-6-[3'-(R,S)amino-4'-hydroxy-butan-1-one]-2,3-dihydro-4H-1-benzopyran-4-one or an analog thereof to the animal such that the 5-amino-2,2-dimethyl-6-[3'-(R,S)amino-4'-hydroxy-butan-1-one]-2,3-dihydro-4H-1-benzopyran-4-one or an analog thereof accumulates in the diseased skin cells; and
   exposing light energy to the diseased cells containing 5-amino-2,2-dimethyl-6-[3'-(R,S)amino-4'-hydroxy-butan-1-one]-2,3-dihydro-4H-1-benzopyran-4-one or an analog thereof, wherein the light energy comprises ultraviolet light provided from any commercially available light source, wherein the ultraviolet light has a wavelength of from about 3665 nm to about 385 nm, and wherein the skin disease is psoriasis.

2. The method as in claim 1, wherein the light energy has an energy of 3 eV to 124 eV.

3. The method of claim 1, wherein the diseased cells containing 5-amino-2,2-dimethyl-6-[3'-(R,S)amino-4'-hydroxy-butan-1-one]-2,3-dihydro-4H-1-benzopyran-4-one or an analog thereof are exposed to light energy for about 2 minutes to about 10 minutes.

4. The method as in claim 1, wherein the 5-amino-2,2-dimethyl-6-[3'-(R,S)amino-4'-hydroxy-butan-1-one]-2,3-dihydro-4H-1-benzopyran-4-one or an analog thereof is administered in an amount of about 0.2 µg to about 200 g.

5. The method as in claim 1, wherein the animal is a human.

6. A method of photodynamic therapy to treat a skin disease in an animal in need thereof, comprising:
   administering 5-amino-2,2-dimethyl-6-[3'-(R,S)amino-4'-hydroxy-butan-1-one]-2,3-dihydro-4H-1-benzopyran-4-one or an analog thereof to the animal such that the 5-amino-2,2-dimethyl-6-[3'-(R,S)amino-4'-hydroxy-butan-1-one]-2,3-dihydro-4H-1-benzopyran-4-one or an analog thereof accumulates in the diseased skin cells; and
   exposing light energy to the diseased cells containing 5-amino-2,2-dimethyl-6-[3'-(R,S)amino-4'-hydroxy-butan-1-one]-2,3-dihydro-4H-1-benzopyran-4-one or an analog thereof, wherein the light energy consists of ultraviolet light, wherein the ultraviolet light has a wavelength of from about 365 nm to about 385 nm, and wherein the skin disease is psoriasis.

7. The method as in claim 6, wherein the light energy has an energy of 3 eV to 124 eV.

* * * * *